US00PP36910P2

(12) United States Plant Patent
Bacon et al.

(10) Patent No.: US PP36,910 P2
(45) Date of Patent: Sep. 2, 2025

(54) GRAPEVINE PLANT NAMED 'SUGRA68'

(50) Latin Name: *Vitis vinifera*
Varietal Denomination: SUGRA68

(71) Applicant: Sun World International, LLC, Wasco, CA (US)

(72) Inventors: Terry A. Bacon, Maplewood, NJ (US); Terrence J. Frett, Bakersfield, CA (US)

(73) Assignee: Sun World International, LLC, Wasco, CA (US)

( * ) Notice: Subject to any disclaimer, the term of this patent is extended or adjusted under 35 U.S.C. 154(b) by 0 days.

(21) Appl. No.: 19/042,944

(22) Filed: Jan. 31, 2025

(30) Foreign Application Priority Data

Mar. 22, 2024 (PE) ..... 542-2024/DIN

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./156, 205
See application file for complete search history.

(56) References Cited

U.S. PATENT DOCUMENTS

PP21,664 P3 * 1/2011 Cain ..... A01H 6/88
Plt./308

* cited by examiner

*Primary Examiner* — Karen M Redden
(74) *Attorney, Agent, or Firm* — Knobbe, Martens, Olson & Bear, LLP

(57) ABSTRACT

The new variety of grapevine 'SUGRA68' is characterized by the production of a large-sized, dark red violet and cylindrical berry with an early season ripening date. The berries of 'SUGRA68' are moderately firm and juicy.

1 Drawing Sheet

Latin name of the genus and species claimed: *Vitis vinifera.*

Variety denomination: 'SUGRA68'.

CROSS-REFERENCE TO RELATED APPLICATIONS

This application claims the benefit of Peruvian Application No. 542-2024/DIN, filed on Mar. 22, 2024, which is incorporated by reference herein in its entirety.

BACKGROUND AND SUMMARY

This application relates to the discovery and asexual propagation of a new and distinct variety of grapevine, 'SUGRA68', as herein described and illustrated. The new variety was first selected as breeder number 'GR946R' by Terry A. Bacon and Terrence J. Frett in Wasco, Kern County, California in July 2020. The variety was originated by controlled hybridization.

The new variety 'SUGRA68' is characterized by the production of a large-sized, dark red violet and cylindrical berry with an early season ripening date. The berries of 'SUGRA68' are firm and juicy.

The seed parent is 'GR458R' (unpatented) and the pollen parent is a bulk pollen mixture of two patented and one unpatented breeding selections: 'Sugrafiftyseven' (U.S. Plant Pat. No. 32,756), 'Sugrafiftyeight' (U.S. Plant Pat. No. 32,666), and 'GR617R' (unpatented). The parent varieties were first crossed in April 2018. The date of first sowing was March 2019, and the date of first flowering was April 2020.

The new variety 'SUGRA68' was first asexually propagated in December 2020 in Wasco, Kern County, California, by Terry A. Bacon and Terrence J. Frett using cuttings and grafting.

The berries of the new variety 'SUGRA68' begin ripening about the same time as its seed parent 'GR458R' (unpatented), but the berries of the new variety 'SUGRA68' have a cylindrical shape compared to a narrow elliptic berry shape for 'GR458R'. Additionally, the new variety 'SUGRA68' has a larger berry weight at 8.3 g and a larger cluster weight at 675 g compared to a berry weight of 6.5 g and a cluster weight of 550 g for 'GR458R'.

The new variety 'SUGRA68' is distinguishable from each of the three red grape varieties of the bulk pollen parent: 'Sugrafiftyseven' (U.S. Plant Pat. No. 32,756), 'Sugrafiftyeight' (U.S. Plant Pat. No. 32,666), and 'GR617R' (unpatented). The fruit of the new variety 'SUGRA68' has a cluster weight of 675 g and a berry weight of 8.3 g, compared to a cluster weight of 700 g and a berry weight of 6.7 g for 'Sugrafiftyseven', a cluster weight of 550 g and a berry weight of 7 g for 'Sugrafiftyeight', and a cluster weight of 750 g and a berry weight of 7.1 g for 'GR617R'. Additionally, the new variety 'SUGRA68' has cylindrical shaped berries like 'Sugrafiftyeight', compared to the broad elliptic berry shape of 'Sugrafiftyseven' and 'GR617R'. The berries of the new variety 'SUGRA68' are dark red violet in color compared to the red colored berries of 'Sugrafiftyseven', 'Sugrafiftyeight' and 'GR617R'. Further, the berries of the new variety 'SUGRA68' begin ripening about July 8, compared to July 11 for 'Sugrafiftyseven', July 4 for 'Sugrafiftyeight', and July 16 for 'GR617R'.

The fruit of the new variety 'SUGRA68' begins ripening at about the same time as 'Flame Seedless' (unpatented), but the berries of the new variety 'SUGRA68' have a weight of 8.3 g compared to a berry weight of 4.8 g for 'Flame Seedless'. Additionally, the berry shape of the new variety 'SUGRA68' is cylindrical compared to globose for 'Flame Seedless'.

The fruit of the new variety 'SUGRA68' has rudimentary seed traces like 'Sheegene-12' (U.S. Plant Pat. No. 20,252), but the ripening of the fruit of the new variety 'SUGRA68' begins about July 8 compared to August 1 for 'Sheegene-12'. Additionally, the berry shape for the new variety 'SUGRA68' is cylindrical compared to the ovate berry shape of 'Sheegene-12'.

The fruit of the new variety 'SUGRA68' has rudimentary seed traces like that of 'IFG 68-175' (U.S. Plant Pat. No. 21,664), but the berry shape is cylindrical for 'SUGRA68' compared to broad ellipsoid for 'IFG 68-175'. Further, the fruit of the new variety 'SUGRA68' begins ripening about July 8 compared to August 10 for 'IFG 68-175'.

The new variety 'SUGRA68' has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration taken from a 3-year-old plant shows typical specimens of the foliage and fruit of the new grape variety 'SUGRA68'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, sixth edition, 2015.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three-year-old 'SUGRA68' plants grown in the vicinity of Wasco, Kern County, California during 2022, and is believed to apply to plants of the variety grown under similar conditions of soil and climate elsewhere.

VINE

General: (Measurements taken on a three-year-old plant).

- *Vine size.*—Large. Height: Approximately 2.0 m. Width: Approximately 2.5 m.
- *Vigor.*—Medium vigor.
- *Density of foliage.*—Dense.
- *Productivity.*—Very productive.
- *Crop load.*—Approximately 30 kg per vine after thinning.
- *Own root.*—Yes.
- *Training method.*—Typically spur pruned leaving 40 2-bud spurs.
- *Resistance.*—Neither resistance nor susceptibility to particular diseases or pests has been observed in this variety.

Trunk:

- *Shape.*—Stocky.
- *Diameter.*—Approximately 4.4 cm (at 30 cm above the soil line).
- *Straps.*—Short.
- *Surface texture.*—Medium shaggy.
- *Inner and Outer bark color.*—Inner bark about Medium Greyed-Orange 166C and weathering to about Dark Greyed-Green 197B in the outer bark.

SHOOTS

Young shoot:

- *Form of tip.*—Wide open.
- *Intensity of anthocyanin coloration of tip.*—Absent or very weak.
- *Density of prostrate hairs on tip.*—Medium.
- *Density of erect hairs on tip.*—Absent or very sparse.
- *Color.*—About Medium Green 141C.

Woody shoot (observations made in the middle third of shoot):

- *Attitude before tying.*—Semi-drooping.
- *Growth of axillary shoots.*—Medium, about 18 cm in length.
- *Internode length.*—Short, approximately 80 mm.
- *Width at node.*—Approximately 10 mm.
- *Cross section.*—Circular.
- *Surface texture.*—Striate.
- *Main color.*—About Medium Greyed-Orange 166C.
- *Color of dorsal side of internode.*—About Medium Greyed-Orange 166C.
- *Color of ventral side of internode.*—About Medium Greyed-Orange 166C.
- *Color of dorsal side of node.*—About Medium Greyed-Orange 166C and Medium Greyed-Orange 166B.
- *Color of ventral side of node.*—About Medium Greyed-Orange 166C and Medium Greyed-Orange 166B.
- *Density of erect hairs on nodes.*—Absent.
- *Density of erect hairs on internodes.*—Absent or Very Sparse.
- *Density of prostrate hairs on internodes.*—Absent or Very Sparse.
- *Density of prostrate hairs on nodes.*—Absent or Very Sparse.

Tendrils:

- *Distribution on the shoot at full flowering.*—Discontinuous.
- *Thickness.*—Approximately 2 mm.
- *Color.*—About Light Green 141D.

*Form*.—Bifurcated.
*Number of consecutive tendrils*.—Up to 2.
*Length of tendril*.—Medium, approximately 15 cm.

LEAVES

Young leaves:
*Color of upper surface of first* 4 *distal unfolded leaves*.—Mixture of Medium Yellow-Green 148B, Medium Greyed-Red 178D and Medium Yellow-Green N144C near the border.
*Average intensity of anthocyanin coloration of six distal leaves prior to flowering*.—Present, covers about 80% of the leaves.
*Density of prostrate hairs between veins at lower surface of* 4*th distal unfolded leaf*.—Absent or very sparse.
*Density of erect hairs between veins at lower surface of* 4*th distal unfolded leaf*.—Absent or very sparse.
*Density of prostrate hairs on veins at lower surface of* 4*th distal unfolded leaf*.—Absent or very sparse.
*Density of erect hairs on veins at lower surface of* 4*th distal unfolded leaf*.—Absent or very sparse.
Mature leaves (observations made in the middle third of shoot):
*Size*.—Large.
*Average length*.—Approximately 11 cm.
*Average width*.—Approximately 14 cm.
*Shape of blade*.—Pentagonal.
*Number of lobes*.—Approximately 5.
*Mature leaf profile*.—Undulate.
*Blistering surface of blade upper surface*.—Absent or very weak.
*Leaf blade tip*.—In the plane of the leaf.
*Undulation of margin*.—Slightly undulating.
*Thickness*.—Average-typical of *Vitis vinifera* species.
*Overall shape of teeth*.—Mixture of both sides straight and both sides convex.
*Length of teeth*.—Medium, ranging from about 5 mm to 10 mm.
*Ratio length/width of teeth*.—Very small, nearly 1:1.
*General shape of petiole sinus lobes*.—Half open.
*Tooth at petiole sinus*.—Absent.
*Petiole sinus limited by veins*.—Absent.
*Shape of upper lateral sinus lobes*.—Slightly overlapping.
*Depth of upper lateral sinuses*.—Shallow, approximately 2 cm to 3 cm.
*Density of prostrate hairs between veins on lower surface of blade*.—Absent to very sparse.
*Density of erect hairs between veins on lower surface of blade*.—Absent to very sparse.
*Density of prostrate hairs on main veins on lower surface of blade*.—Absent to very sparse.
*Density of erect hairs on main veins on lower surface of blade*.—Absent to very sparse.
*Density of prostrate hairs on main veins on upper surface of blade*.—Absent to very sparse.
*Autumn coloration of leaves*.—Usually about Light Green 138B becoming about Medium Grey-Brown 199C.
Upper leaf surface:
*Color*.—About Dark Green 141A.
*Surface texture*.—Smooth.
*Surface appearance*.—Dull.
*Anthocyanin coloration of main veins*.—Absent or very sparse.
Lower leaf surface:
*Color*.—About Medium Green 140B.
*Surface texture*.—Smooth.
*Surface appearance*.—Dull.
*Anthocyanin coloration of main veins*.—Absent or very sparse.
Petiole:
*Length of petiole*.—Approximately 7 cm.
*Diameter*.—Approximately 3 mm.
*Length of petiole compared to middle vein*.—Slightly shorter, 7 cm for the petiole compared to 11 cm for middle vein.
*Density of prostrate hairs on petiole*.—Absent.
*Density of erect hairs on petiole*.—Absent.
*Color*.—About Medium Yellow-Green N144C.
Buds:
*Shape*.—Conical.
*Size*.—Medium, approximately 3 mm wide×4 mm long.
*Position*.—Slightly held out.
*Bud fruitfulness*.—Basal, mostly fruitful.
*Time of bud burst*.—Early, approximately March 15th for the southern San Joaquin Valley region of California.

FLOWERS

General:
*Flower type*.—Fully developed stamen and fully developed gynoecium.
*Position of first flowering node*.—Usually 5th node of current season growth.
*Number of inflorescences per shoot*.—Usually 1.5 per shoot.
*Time of full bloom*.—Approximately May 2nd in the southern San Joaquin Valley region of California.

FRUIT

General:
*Ripening period*.—Early season, beginning about July 8th in the southern San Joaquin Valley region of California.
*Use*.—Fresh market.
*Storage quality*.—Good.
Cluster:
*Form*.—Broadly conical, shouldred.
*Cluster size* (*peduncle excluded*).—Large.
*Cluster length* (*peduncle excluded*).—Approximately 24 cm.
*Cluster width*.—Approximately 17 cm.
*Cluster weight*.—Approximately 675 g.
*Cluster density*.—Loose, some visible pedicels.
*Number of berries*.—Approximately 90 berries after tipping.
Peduncle:
*Length*.—Medium, approximately 5 cm.
*Diameter*.—Approximately 8 mm.
*Lignification of peduncle*.—Weak.
*Color*.—About Medium Green 143B.
Berry:
*Size*.—Large, approximately 8.3 g.
*Dimensions*.—Width: Approximately 22 mm. Length: Approximately 33 mm.

*Uniformity of size*.—Uniform.
*Shape*.—Cylindrical.
*Cross section*.—Circular.
*Skin color* (*without bloom*).—About Dark Purple N77A.
*Flesh color*.—About Light Green 138C and Medium Green 139C.
*Anthocyanin color of flesh*.—Absent or very weak.
*Bloom* (*cuticular wax*).—Medium, typical of most commercial *Vitis vinifera*.
*Pedicel length*.—Approximately 20 mm.
*Pedicel thickness*.—Medium, approximately 1.9 mm.
*Berry separation from pedicel*.—Moderately easy.
*Seed traces*.—Rudimentary.
*Berry firmness*.—Moderately firm.
*Flesh juiciness*.—Juicy.
*Flesh texture*.—Firm and meaty.
*Particular flavor*.—Tropical.
*Refractometer test*.—About 22 Brix.
*Juice pH*.—About 3.21.
*Titratable acidity*.—About 0.54%.
*Brix*.—Acid Ratio: Approximately 40.7.

Skin:
*Skin thickness*.—Medium, about 175 μm.
*Skin texture*.—Smooth.
*Skin reticulation*.—Absent.
*Skin tenacity*.—Tenacious to flesh.
*Skin tendency to crack*.—Rare.
*Skin sensitivity to sunburn*.—None.

What is claimed is:

1. A new and distinct variety of grapevine plant named 'SUGRA68', substantially as illustrated and described herein.

* * * * *

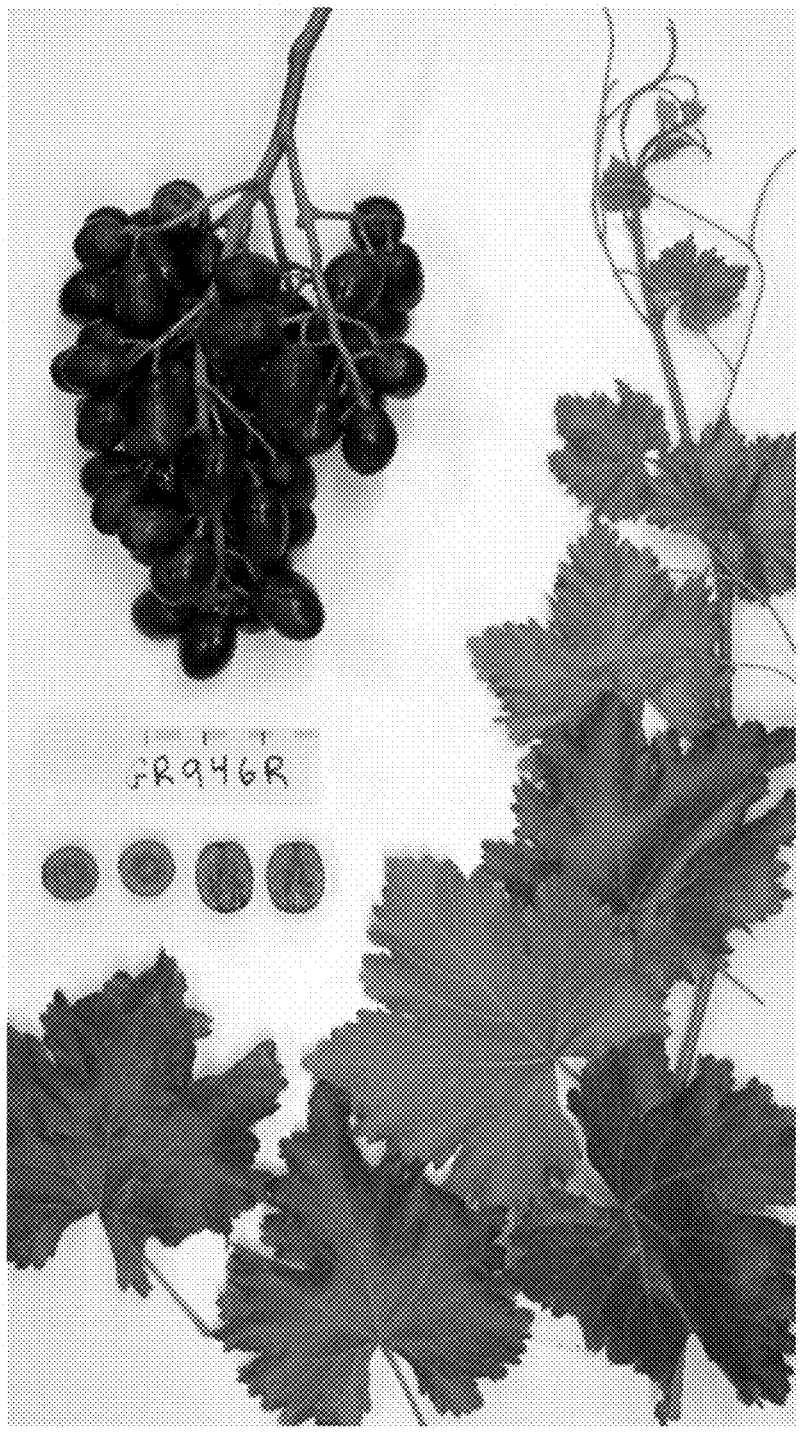
FR946R